United States Patent [19]

Wright, Jr. et al.

[11] 4,200,748
[45] Apr. 29, 1980

[54] PYRIDO[1',2':4,5][1,4]OXAZINO[2,3-b]QUINOXALINES AND PYRROLO[1',2':4,5][1,4]OXAZINO[2,3-b]QUINOXALINES

[75] Inventors: William B. Wright, Jr., Woodcliff Lake; Andrew S. Tomcufcik, Old Tappan, both of N.J.

[73] Assignee: American Cyanamid Company, Stamford, Conn.

[21] Appl. No.: 5,411

[22] Filed: Jan. 22, 1979

[51] Int. Cl.² .......................................... C07D 498/04
[52] U.S. Cl. ................................ 544/99; 424/248.4; 424/248.56; 544/356
[58] Field of Search ............................................ 544/99

[56] References Cited

PUBLICATIONS

Winterfeld et al, Chemical Abstracts, vol. 73, Abst. No. 35330s (1970), (Abst. of Arch. Pharm. (Weinheim) vol. 303, 00 391–401, 1970).

*Primary Examiner*—John D. Randolph
*Attorney, Agent, or Firm*—Edward A. Conroy, Jr.

[57] ABSTRACT

This disclosure describes substituted 2,3,3a,4-tetrahydro-1H-pyrrolo[1',2':4,5][1,4]oxazino[2,3-b]quinoxalines and 1,2,3,4,4a,5-hexahydropyrido[1',2':4,5][1,4]oxazino[2,3-b]quinoxalines which possess anxioyltic activity.

12 Claims, No Drawings

PYRIDO[1',2':4,5][1,4]OXAZINO[2,3-b]QUINOXALINES AND PYRROLO[1',2':4,5][1,4]OXAZINO[2,3-b]QUINOXALINES

BRIEF SUMMARY OF THE INVENTION

This invention relates to new organic compounds and, more particularly, is concerned with novel substituted 2,3,3a,4-tetrahydro-1H-pyrrolo[1',2':4,5][1,4]oxazino[2,3-b]quinoxalines (I) and 1,2,3,4,4a,5-hexahydropyrido[1',2':4,5][1,4]oxazino[2,3-b]quinoxalines (II) which may be represented by the following structural formulae:

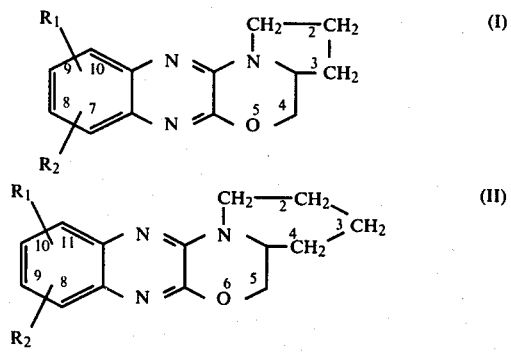

wherein $R_1$ and $R_2$ are each individually selected from the group consisting of hydrogen, fluoro, chloro, bromo, trifluoromethyl, alkyl having from 1 to 4 carbon atoms, alkoxy having from 1 to 4 carbon atoms, nitro, amino, alkanoylamino having from 2 to 4 carbon atoms, benzoylamino and dimethylformamidino.

DETAILED DESCRIPTION OF THE INVENTION

The novel compounds of the present invention are obtainable as colorless to yellow crystalline materials having characteristic melting points and absorption spectra. They are appreciably soluble in many organic solvents such as lower alkanols, chloroform, tetrahydrofuran, N,N-dimethylformamide and the like but are generally insoluble in water.

The organic bases of this invention form non-toxic acid-addition salts with a variety of pharmacologically acceptable organic and inorganic salt-forming reagents. Thus, acid-addition salts, formed by admixture of the organic free base with one or more equivalents of an acid, suitably in a neutral solvent, are formed with such acids as sulfuric, phosphoric, hydrochloric, hydrobromic, sulfamic, citric, lactic, malic, succinic, tartaric, acetic, benzoic, gluconic, ascorbic, and the like. For purposes of this invention, the free bases are equivalent to their non-toxic acid-addition salts. The acid-addition salts of the organic bases of the present invention are, in general, crystalline solids, relatively soluble in water, methanol and ethanol but relatively insoluble in non-polar organic solvents such as diethyl ether, benzene, toluene, and the like.

Certain of the novel compounds of the present invention may be readily prepared as set forth in the following reaction scheme:

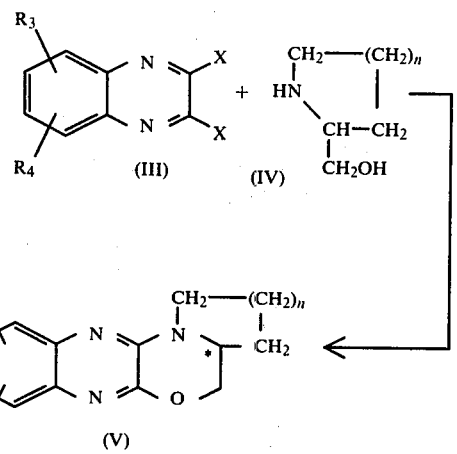

wherein n is the integer 1 or 2; X is chloro or bromo; and $R_3$ and $R_4$ are each individually selected from the group consisting of hydrogen, fluoro, chloro, bromo, trifluoromethyl, alkyl having from 1 to 4 carbon atoms, alkoxy having from 1 to 4 carbon atoms and nitro. In accordance with this reaction scheme, an appropriately substituted 2,3-dihaloquinoxaline (III) is reacted with 2-pyrrolidinomethanol (IV when n=1) or 2-piperidinomethanol (IV when n=2) to provide the corresponding substituted tetrahydropyrrolo[1',2':4,5][1,4]oxazino[2,3-b]quinoxalines (V when n=1) or hexahydropyrido[1',2':4,5][1,4]oxazino[2,3-b]quinoxalines (V when n=2). This cyclization is carried out in an inert, water miscible, organic solvent such as dioxane, tetrahydrofuran, dimethylformamide, and the like at steam bath temperatures for a period of time of from about four hours to about four days. For best results, the cyclization should be carried out in the presence of an acid-acceptor such as pyridine, triethylamine, soda ash, and the like. Upon dilution of the reaction mixture with water, the products (V) precipitate and may be separated and purified by conventional techniques.

In those cases where the 2,3-dihaloquinoxaline starting materials (III) are unsymmetrically substituted, a mixture of two position isomers of (V) is obtained since the cyclization takes place in both possible ways. For example, 2,3,5,7-tetrabromoquinoxaline gives rise to (7,9-dibromo and 8,10-dibromo)-2,3,3a,4-tetrahydro-1H-pyrrolo[1',2':4,5][1,4]oxazino[2,3-b]quinoxalines (V when n=1) and to (8,10-dibromo and 9,11-dibromo)-1,2,3,4,4a,5-hexahydropyrido[1',2':4,5][1,4]oxazino[2,3-b]quinoxalines (V when n=2). These position isomers may be readily separated by conventional methods such as fractional crystallization and column chromatography. The novel products of the cyclization process also possess an asymmetric center at the 3a-position of the tetrahydropyrrolo derivatives and at the 4a-position of the hexahydropyrido derivatives (designated by an asterisk in formula V) and are thus obtained as racemic mixtures. These racemic mixtures can be resolved into their optically active components by a number of methods of resolution well known in the art. For example, they can be treated with an optically active acid such as (+ or −)-α-methoxy-α-trifluoromethylphenylacetic acid, (+)-10-camphorsulfonic acid or (+)-N-benzoyl-(R)-glutamic acid and the like to produce diastereoisomeric salts which can be separated by crystallization.

Resolution can also be accomplished by reverse phase and absorption chromatography on an optically active support and adsorbent and by selective transformation of one isomer with a biologically-active transforming system.

The novel compounds of formulae (I) and (II) wherein $R_1$ and/or $R_2$ are amino are prepared by the catalytic reduction of the novel compounds of formula (V) wherein $R_3$ and/or $R_4$ are nitro. This catalytic reduction is achieved in a solvent for the starting material in the presence of a metal catalyst and hydrogen gas at pressures from atmospheric to super-atmospheric. Ordinarily, the catalytic reduction is conveniently carried out at hydrogen pressures of from about one to about four atmospheres. Temperature does not appear to be critical in the catalytic hydrogenation. Temperatures of from 0° C. to 50° C., and usually room temperature, are preferred since they generally give best results. The metal catalyst may be of the base metal type, such as nickel or copper chromite, or it may be of the noble metal type, such as finely divided platinum, palladium or rhodium. The noble metal catalysts are advantageously employed on a carrier such as finely divided alumina, activated charcoal, diatomaceous earth, etc., in which form they are commonly available. The hydrogenation is carried out until the desired amount of hydrogen gas is absorbed at which point the hydrogenation is stopped. The solvents selected for the catalytic reduction should be reaction-inert, that is, they should not be capable of reacting with the starting materials, product, or hydrogen under the conditions of the reaction. A variety of solvents may be used for this purpose and minimum laboratory experimentation will permit the selection of a suitable solvent for any specific starting compound. Generally, the catalytic hydrogenation may be carried out in solvents such as water, lower alkanols, e.g. methanol, ethanol; lower alkoxy lower alkanols, e.g. 2-methoxyethanol, 2-ethoxyethanol; tetrahydrofuran, dioxane, dimethylformamide, etc.

The acylation of the monoamino and diamino derivatives of formulae (I) and (II) is accomplished by treatment with benzoyl chloride or with either an alkanoic acid halide or an alkanoic acid anhydride of the formulae:

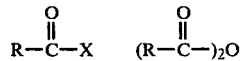

wherein R is alkyl having from 1 to 3 carbon atoms and X is as hereinabove defined. This acylation may be carried out either in an inert organic solvent such as chloroform or dioxane or in an excess of the acylating agent as solvent at from room temperature to steam bath temperatures for a period of time of 1–12 hours. Where the acylating agent is an acid halide, then an acid-acceptor such as triethylamine, soda ash or dilute aqueous caustic may advantageously be employed. The preparation of the dimethylformamidino derivatives is readily accomplished by treatment of the monoamino and diamino starting materials of formulae (I) and (II) with an excess of dimethylformamide dimethylacetal at the reflux temperature for a period of 4–8 hours.

The novel compounds of the present invention possess central nervous system activity at non-toxic doses and as such are useful as anxiolytic agents. That is, they produce certain responses in standard tests with laboratory animals which are known to correlate well with relief of anxiety in man. The compounds have been tested pharmacologically and found to have such properties with a desirable wide spread between doses producing anxiolytic activity and toxic symptoms.

A test used to measure anxiolytic activity comprises measurement of the ability of test compounds to inhibit the binding of $^3$H-diazepam to the brain receptors of warm-blooded animals. The test is described by R. F. Squires in Nature, 266, No. 21, page 732 (April 1977). The animals used were male albino rats of the Wistar strain, weighing 150–200 g. each from Royalhart Farms. Diazepam (methyl-$^3$H) was obtained from New England Nuclear. The test compounds were solubilized in either dimethylformamide, acetic acid, ethanol or hydrochloric acid. The frontal cortex of rats was homogenized gently in 20 volumes of ice-cold 0.32 M. sucrose, centrifuged twice at 1000 g. for 10 minutes and then recentrifuged at 30,000 g. for 20 minutes to produce a crude $P_2$-synaptosomal fraction. The $P_2$-fraction was rehomogenised, twice the original volume, in hypotonic 50 mM. Tris.HCl (pH 7.4). The binding assay consisted of 300 $\mu$l. of the $P_2$-fraction suspension (0.350 mg.), 100 $\mu$l. of test drug and 100 $\mu$l. of $^3$H-diazepam (1.5 nM.), which was added to 1.5 ml. of 50 mM. Tris.HCl (pH 7.4). Non-specific binding controls and total binding controls received 100 $\mu$l. of diazepam (3 $\mu$m.) and 100 $\mu$l. of deionized water, respectively, in place of the test compound. Incubation for 20 minutes proceeded in ice and was terminated by filtration, under vacuum, through Whatman GF/C glass fiber filters. The filters were washed twice with 5 ml. of ice-cold 50 mM. Tris.HCl (pH 7.4) and placed in scintillation vials. After drying at 50°–60° C. for 30 minutes, 10 ml. of Beckman Ready-Solve HP was added and the radioactivity determined in a Beckman Scintillation Counter.

The results of this test with typical compounds of this invention appear in Table I below:

Table I

| Compound | % Inhibition of Diazepam Binding | $IC_{50}$ nM. |
|---|---|---|
| 9-Chloro-1,2,3,4,4a,5-hexahydropyrido[1',2':4,5][1,4]oxazino[2,3-b]quinoxaline | 97 | 14 |
| 10-Chloro-1,2,3,4,4a,5-hexahydropyrido[1',2':4,5][1,4]oxazino[2,3-b]quinoxaline | 95 | 22 |
| 11-Amino-1,2,3,4,4a,5-hexahydropyrido[1',2':4,5][1,4]oxazino[2,3-b]quinoxaline | 98 | 20 |
| 9-Amino-1,2,3,4,4a,5-hexahydropyrido[1',2':4,5][1,4]oxazino[2,3-b]quinoxaline | 93 | 39 |
| N'-(1,2,3,4,4a,5-Hexahydropyrido[1',2':4,5][1,4]oxazino[2,3-b]quinoxalin-11-yl)-N,N-dimethylformamidine | 96 | 55 |
| 1,2,3,4,4a,5-Hexahydro-11-nitropyrido[1',2':4,5][1,4]oxazino[2,3-b]quinoxaline | 72 | 210 |
| 1,2,3,4,4a,5-Hexahydro-9-trifluoromethylpyrido[1',2':4,5][1,4]oxazino[2,3-b]quinoxaline | 90 | 352 |

Table I-continued

| Compound | % Inhibition of Diazepam Binding | IC$_{50}$ nM. |
|---|---|---|
| 2,3,3a,4-Tetrahydro-1H-pyrrolo[1',2':4,5][1,4]oxazino[2,3-b]-quinoxaline | 87 | 87 |

The novel compounds of the present invention have thus been found to be highly useful for meliorating anxiety in mammals when administered in amounts ranging from about 0.03 mg. to about 10.0 mg./kg. of body weight per day. A preferred dosage regimen for optimum results would be from about 0.1 mg. to about 5.0 mg./kg. of body weight per day. Such dosage units are employed that a total of from about 7.0 mg. to about 350 mg. of active compound for a subject of about 70 kg. of body weight are administered in a 24 hour period. This dosage regimen may be adjusted to provide the optimum therapeutic response. For example, several divided doses may be administered dialy or the dose may be proportionally reduced as indicated by the exigencies of the therapeutic situation. A decided practical advantage of this invention is that the active compounds may be administered in any convenient manner such as by the oral, intravenous, intramuscular, or subcutaneous routes.

Compositions according to the present invention having the desired clarity, stability and adaptability for parenteral use are obtained by dissolving from 0.10% to 10.0% by weight of active compound in a vehicle consisting of a polyhydric aliphatic alcohol or mixtures thereof. Especially satisfactory are glycerin, propylene glycol, and polyethylene glycols. The polyethylene glycols consist of a mixture of non-volatile, normally liquid, polyethylene glycols which are soluble in both water and organic liquids and which have molecular weights of from about 200 to 1500. Although the amount of active compound dissolved in the above vehicle may vary from 0.10 to 10.0% by weight, it is preferred that the amount of active compound employed be from about 3.0 to about 9.0% by weight. Although various mixtures of the aforementioned non-volatile polyethylene glycols may be employed, it is preferred to use a mixture having an average molecular weight of from about 200 to about 400.

In addition to the active compound, the parenteral solutions may also contain various preservatives which may be used to prevent bacterial and fungal contamination. The preservatives which may be used for these purposes are, for example, myristyl-gamma-picolinium chloride, benzalkonium chloride, phenethyl alcohol, p-chlorophenyl-α-glycerol ether, methyl and propyl parabens, and thimerosal. As a practical matter, it is also convenient to employ antioxidants. Suitable antioxidants include, for example, sodium bisulfite, sodium metabisulfite, and sodium formaldehyde sulfoxylate. Generally, from about 0.05 to about 0.2% concentrations of antioxidant are employed.

The active compounds of the present invention may be orally administered, for example, with an inert diluent or with an assimilable edible carrier, or they may be enclosed in hard or soft shell gelatin capsules, or they may be compressed into tablets, or they may be incorporated directly with the food of the diet. For oral therapeutic administration, the active compounds may be incorporated with excipients and used in the form of tablets, troches, capsules, suspensions, syrups, wafers, and the like. Such compositions and preparations should contain at least 0.1% of active compound. The precentage of the compositions and preparations may, of course, be varied and may conveniently be between about 2% to about 60% of the weight of the unit. The amount of active compound in such therapeutically useful compositions is such that a suitable dosage will be obtained. Preferred compositions or preparations according to the present invention are prepared so that an oral dosage unit form contains between about 5 and 200 milligrams of active compound.

The tablets, troches, pills, capsules and the like may also contain the following: a binder such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, lactose or saccharin may be added or a flavoring agent such as peppermint, oil of wintergreen, or cherry flavoring. When the dosage unit form is a capsule, it may contain, in addition to materials of the above type, a liquid carrier such as a fatty oil. Various other materials may be present as coatings or to otherwise modify the physical form of the dosage unit. For instance, tablets, pills, or capsules may be coated with shellac, sugar or both. A syrup may contain the active compound, sucrose as a sweetening agent, methyl and propylparabens as preservatives, a dye and flavoring such as cherry or orange flavor. Of course, any material used in preparing any dosage unit form should be pharmaceutically pure and substantially non-toxic in the amounts employed.

A preferred embodiment of the present invention may be represented by the following structural formula:

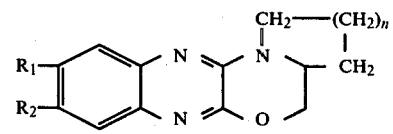

wherein n, R$_1$ and R$_2$ are as hereinbefore defined and the non-toxic acid-addition salts thereof.

This invention will be described in greater detail in conjunction with the following specific examples. The following examples are given for the purpose of illustration and are not intended to limit the scope of the invention.

EXAMPLE 1

1,2,3,4,4a,5-Hexahydropyrido[1',2':4,5][1,4]oxazino[2,3-b]quinoxaline

A mixture of 20 g. of 2,3-dichloroquinoxaline, 13.8 g. of 2-piperidinomethanol, 40 ml. of triethylamine and 200 ml. of dimethylformamide is heated on a steam bath for 44 hours and then diluted with 400 ml. of water. The solid is collected by filtration, washed with water and air dried. This solid is dissolved in dichloromethane, passed through Magnesol ® and recrystallized from ethyl acetate, giving the desired product as yellow crystals, m.p. 141°–143° C.

The monohydrochloride salt is prepared by treatment of the base compound dissolved in ethanol with ethanolic hydrogen chloride and melts at about 300° C.

EXAMPLE 2

9-Chloro-1,2,3,4,4a,5-hexahydropyrido[1',2':4,5][1,4]oxazino[2,3-b]quinoxaline and 10-chloro-1,2,3,4,4a,5-hexahydropyrido[1',2':4,5][1,4]oxazino[2,3-b]quinoxaline A mixture of 23.3 g. of 2,3,6-trichloroquinoxaline, 11.5 g. of 2-piperidinomethanol, 40 ml. of triethylamine and 400 ml. of dimethylformamide is stirred at room temperature for 4 hours and then heated on a steam bath for 48 hours. A 500 ml. portion of water is added dropwise. The solid is recovered by filtration, washed with water and air dried. This solid is dissolved in dichloromethane, passed through Magnesol ® and recrystallized from ethyl acetate. Recrystallization from ethanol or ethyl acetate gives pale yellow crystals of 10-chloro-1,2,3,4,4a,5-hexahydropyrido[1',2':4,5][1,4]oxazino[2,3-b]quinoxaline, m.p. 147°–149° C.

Fractional crystallization from the mother liquor gives a second yield of the above 10-chloro derivative plus 9-chloro-1,2,3,4,4a,5-hexahydropyrido[1',2':4,5][1,4]oxazino[2,3-b]quinoxaline, m.p. 107°–109° C.

The monohydrochloride salts of both compounds may be prepared as described in Example 1 and decompose above 300° C.

EXAMPLE 3

1,2,3,4,4a,5-Hexahydro-11-nitropyrido[1',2':4,5][1,4]oxazino[2,3-b]quinoxaline and 1,2,3,4,4a,5-hexahydro-8-nitropyrido[1',2':4,5][1,4]oxazino[2,3-b]quinoxaline A mixture of 24.4 g. of 2,3-dichloro-5-nitroquinoxaline, 12.4 g. of 2-piperidinomethanol, 40 ml. of triethylamine and 400 ml. of dimethylformamide is stirred at room temperature for 4 hours, heated on a steam bath for 48 hours, diluted with 600 ml. of water, cooled overnight and filtered. The solid is dissolved in dichloromethane, passed through Magnesol ® and recrystallized from ethyl acetate giving 1,2,3,4,4a,5-hexahydro-11-nitropyrido[1',2':4,5][1,4]oxazino[2,3-b]quinoxaline as yellow crystals, m.p. 182°–184° C.

Partion chromatography of the mother liquor gave 1,2,3,4,4a,5-hexahydro-8-nitropyrido[1',2':4,5][1,4]oxazino[2,3-b]quinoxaline, m.p. 205°–207° C.

EXAMPLE 4

1,2,3,4,4a,5-Hexahydro-9-nitropyrido[1',2':4,5][1,4]oxazino[2,3-b]quinoxaline and 1,2,3,4,4a,5-hexahydro-10-nitropyrido[1',2':4,5][1,4]oxazino[2,3-b]quinoxaline A mixture of 36.6 g. of 6-nitro-2,3-dichloroquinoxaline, 17.3 g. of 2-piperidinomethanol, 60 ml. of triethylamine and 500 ml. of dimethylformamide is stirred at room temperature for 4 hours, heated on a steam bath for 48 hours, diluted with 700 ml. of water and cooled overnight. The water is decanted and the residue taken up in dichloromethane, washed with water and passed through Magnesol ®. The filtrate is concentrated to an oil which is dissolved in 150 ml. of ethyl acetate and cooled. The resulting crystals are recovered by filtration and recrystallized from ethyl acetate giving 1,2,3,4,4a,5-hexahydro-9-nitropyrido[1',2':4,5][1,4]oxazino[2,3-b]quinoxaline, m.p. 151°–154° C.

The mother liquor from the first precipitation is concentrated to remove the solvent and then triturated with ether to provide a second fraction. This second fraction is boiled with the mother liquor from the first fraction providing as insoluble matter 1,2,3,4,4a,5-hexahydro-10-nitropyrido[1',2':4,5][1,4]oxazino[2,3-b]quinoxaline, m.p. 226°–229° C.

EXAMPLE 5

9-Amino-1,2,3,4,4a,5-hexahydropyrido[1',2':4,5][1,4]oxazino[2,3-b]quinoxaline

A mixture of 5.72 g. of 1,2,3,4,4a,5-hexahydro-9-nitropyrido[1',2':4,5][1,4]oxazino[2,3-b]quinoxaline, 200 ml. of dioxane and 1.5 g. of palladium on carbon catalyst is shaken in a Parr hydrogenator under 45 lb. of hydrogen pressure until reduction is complete. The mixture is filtered and the filtrate concentrated to a residue. The residue is recrystallized from ethanol to give the desired product, m.p. 229°–232° C.

EXAMPLE 6

11-Amino-1,2,3,4,4a,5-hexahydropyrido[1',2':4,5][1,4]oxazino[2,3-b]quinoxaline

A 5.72 g. portion of 1,2,3,4,4a,5-hexahydro-11-nitropyrido[1',2':4,5][1,4]oxazino[2,3-b]quinoxaline is reacted as described in Example 5 to give the desired compound, m.p. 207°–209° C.

EXAMPLE 7

N-(1,2,3,4,4a,5-Hexahydropyrido[1',2':4,5][1,4]oxazino[2,3-b]quinoxalin-9-yl)acetamide and N-(1,2,3,4,4a,5-hexahydropyrido[1',2':4,5][1,4]oxazino[2,3-b]quinoxalin-11-yl)acetamide One part of 9-amino-1,2,3,4,4a,5-hexahydropyrido[1',2':4,5][1,4]oxazino[2,3-b]quinoxaline is mixed with three parts of acetic anhydride producing an exothermic reaction. The mixture is allowed to stand for 4–6 hours then diluted with ether and filtered. The desired product is purified by recrystallization from ethanol, m.p. 245°–247° C.

Substitution of 11-amino-1,2,3,4,4a,5-hexahydropyrido[1',2':5,4][1,4]oxazino[2,3-b]quinoxaline in the above reaction produces the corresponding 11-substituted acetamide, m.p. 257°–261° C.

EXAMPLE 8

N'-(1,2,3,4,4a,5-Hexahydropyrido[1',2':4,5][1,4]oxazino[2,3-b]quinoxalin-9-yl)-N,N-dimethylformamidine and N'-(1,2,3,4,4a,5-hexahydropyrido[1',2':4,5][1,4]oxazino[2,3-b]quinoxalin-11-yl)-N,N-dimethylformamidine A mixture of 0.01 moles of 9-amino-1,2,3,4,4a,5-hexahydropyrido[1',2':4,5][1,4]oxazino[2,3-b]quinoxaline and 8 ml. of dimethylformamide dimethylacetal is heated at reflux for 6 hours. Ether is added and the crystalline product is recovered by filtration, m.p. 186°–188° C.

Substitution of 11-amino-1,2,3,4,4a,5-hexahydropyrido[1',2':4,5][1,4]oxazino[2,3-b]quinoxaline in the above reaction produces the corresponding 11-substituted dimethylformamidine, m.p. 183°–185° C.

EXAMPLE 9

1,2,3,4,4a,5-Hexahydro-9-trifluoromethyl-pyrido[1',2':4,5][1,4]oxazino[2,3-b]quinoxaline A mixture of 10.3 g. of 4-amino-3-nitrobenzotrifluoride, 200 ml. of ethanol and 0.25 g. of platinum oxide catalyst is shaken in a Parr hydrogenator under 45 lb. of hydrogen pressure until reduction is complete. The catalyst is removed by filtration and the solvent removed in vacuo. A 50 ml. portion of diethyloxalate is added to the residue and the mixture is heated at reflux for 2 hours. After cooling the solid is recovered by filtration, washed with ether and dried in vacuo giving 9.5 g. of 6-trifluoromethyl-2,3-quinoxalinediol.

A mixture of 23.0 g. of 6-trifluoromethyl-2,3-quinoxalinediol, 50 g. of phosphorous pentachloride and 10 g. (6 ml.) of phosphorous oxychloride is carefully heated to reflux temperature and held at reflux for 4 hours. The solution is allowed to cool, then poured into ice and water and filtered. The filtrate is extracted into dichloromethane, washed three times with water, dried over magnesium sulfate and concentrated. The residue is triturated with hexane and filtered giving 22.2 g. of 2,3-dichloro-6-trifluoromethylquinoxaline as a cream colored solid.

A mixture comprising 13.4 g. of 2,3-dichloro-6-trifluoromethylquinoxaline, 6.3 g. of 2-piperidinomethanol, 20 ml. of triethylamine and 160 ml. of dimethylformamide is stirred at room temperature for 4 hours and then on a steam bath for 48 hours. A 250 ml. portion of water is added gradually, with cooling. The resulting precipitate is recovered by filtration, washed with water, dissolved in dichloromethane, dried over magnesium sulfate, passed through Magnesol ® and concentrated. The residue is washed onto a filter with ether leaving a solid. This solid is dissolved in 80 ml. of ethanol and then cooled in a refrigerator producing a yellow solid. This solid is recrystallized from 30 ml. of ethyl acetate with refrigeration giving the desired product as a pale yellow solid, m.p. 154°–156° C.

EXAMPLE 10

(+)-2,3,3a,4-Tetrahydro-1H-pyrrolo[1',2':4,5][1,4]oxazino[2,3-b]quinoxaline

A mixture of 4.93 ml. of L-2-pyrrolidinomethanol, 20 ml. of triethylamine, 10.0 g. of 2,3-dichloroquinoxaline and 100 ml. of dimethylformamide is heated on a steam bath for 48 hours. A 200 ml. portion of water is added and the mixture is stored in a freezer for 48 hours. The solid is recovered by filtration, dissolved in dichloromethane, passed through Magnesol ® and concentrated. The residue is dissolved in 15 ml. of ethyl acetate, stored in a freezer for several days, concentrated to a crystalline residue and washed with ether. These crystals are recrystallized from 5 ml. of ethanol, giving the desired product as yellow crystals, m.p. 121°–123° C., $[\alpha]_D^{25} + 114°$ (methanol).

EXAMPLE 11

2,3,3a,4-Tetrahydro-8-nitro-1H-pyrrolo[1',2':4,5][1,4]oxazino[2,3-b]quinoxaline

A 24.4 g. portion of 6-nitro-2,3-dichloroquinoxaline is added in one portion to a mixture of 10.2 g. of L-2-pyrrolidinomethanol, 40 ml. of triethylamine and 400 ml. of dimethylformamide which has been cooled to −5° C. in an ice bath. The mixture is stirred in the ice bath for 5 minutes, then at room temperature for 2 hours, finally on a steam bath overnight. A 500 ml. portion of water is added in increments. The mixture is cooled to room temperature and the solid is collected by filtration, washed with water, then hexane and dried. This solid is boiled in 300 ml. of dichloromethane and then filtered. The filtrate is passed through Magnesol ® and hexane is added giving a solid. The solid is recrystallized from ethyl acetate giving the desired product, m.p. 234°–237° C.

EXAMPLE 12

1,2,3,4,4a,5-Hexahydropyrido[1',2':4,5][1,4]oxazino[2,3-b]quinoxaline

A mixture of 4.0 g. of 2,3-dichloroquinoxaline and 4.84 g. of 2-piperidinomethanol is heated at 120° C. for 3 hours and then treated with 50 ml. of water and 8 ml. of 5 N sodium hydroxide. The solid product is filtered off, washed with water and air dried. Recrystallization from ethyl acetate results in the desired product, m.p. 141°–143° C.

EXAMPLE 13

8-Amino-2,3,3a,4-tetrahydro-1H-pyrrolo[1',2':4,5][1,4]oxazino[2,3-b]quinoxaline

Ten grams of 2,3,3a,4-tetrahydro-8-nitro-1H-pyrrolo[1',2':4,5][1,4]oxazino[2,3-b]quinoxaline (Example 11) is reacted as described in Example 5 to give the desired compound.

EXAMPLE 14

N-(2,3,3a,4-tetrahydro-1H-pyrrolo[1',2':4,5][1,4]oxazino[2,3-b]quinoxalin-8-yl)acetamide This compound is obtained when 8-amino-2,3,3a,4-tetrahydro-1H-pyrrolo[1',2':4,5][1,4]oxazino[2,3-b]quinoxaline is allowed to react with acetic anhydride as described in Example 7.

EXAMPLE 15

8-Chloro-2,3,3a,4-tetrahydro-1H-pyrrolo[1',2':4,5][1,4]oxazino[2,3-b]quinoxaline and
9-chloro-2,3,3a,4-tetrahydro-1H-pyrrolo[1',2':4,5][1,4]oxazino[2,3-b]quinoxaline A mixture of 4.93 g. of 2-pyrrolidinomethanol, 20 ml. of triethylamine, 100 ml. of dimethylformamide and 11.7 g. of 2,3,6-trichloroquinoxaline is stirred at room temperature for 5 hours and then heated on the steam bath for 48 hours. The reaction mixture is diluted with water and extracted twice with dichloromethane. The dichloromethane solution is washed with water, passed through diatomaceous earth and concentrated to remove the solvent. The residue is fractionally recrystallized from ethyl acetate and ethanol and the above named compounds are obtained.

EXAMPLE 16

9-Bromo-1,2,3,4,4a,5-hexahydropyrido[1',2':4,5][1,4]oxazino[2,3-b]quinoxaline and
10-bromo-1,2,3,4,4a,5-hexahydropyrido[1',2':4,5][1,4]oxazino[2,3-b]quinoxaline The above compounds are obtained when 6-bromo-2,3-dichloro quinoxaline is treated with 2-piperidinomethanol by the procedure of Example 2.

EXAMPLE 17

9-Fluoro-1,2,3,4,4a,5-hexahydropyrido[1',2':4,5][1,4]oxazino[2,3-b]quinoxaline and 10-fluoro-1,2,3,4,4a,5-hexahydropyrido[1',2':4,5][1,-4]oxazino[2,3-b]quinoxaline When 2,3-dichloro-6-fluoroquinoxaline is substituted for 2,3,6-trichloroquinoxaline in the procedure of Example 2, the above compounds are obtained.

EXAMPLE 18

1,2,3,4,4a,5-Hexahydro-9-methylpyrido[1',2':4,5][1,-4]oxazino[2,3-b]quinoxaline and 1,2,3,4,4a,5-hexahydro-10-methylpyrido[1',2':4,5][1,-4]oxazino[2,3-b]quinoxaline If 2,3-dichloro-6-methylquinoxaline is treated with 2-piperidinomethanol as described in Example 2, the above compounds are obtained.

EXAMPLE 19

9-Ethyl-1,2,3,4,4a,5-hexahydropyrido[1',2':4,5][1,4]oxazino[2,3-b]quinoxaline and 10-ethyl-1,2,3,4,4a,5-hexahydropyrido[1',2':4,5][1,4]oxazino[2,3-b]quinoxaline These compounds are obtained when 2,3-dichloro-6-ethylquinoxaline is substituted for 2,3,6-trichloroquinoxaline in the procedure of Example 2.

EXAMPLE 20

1,2,3,4,4a,5-hexahydro-9-methoxypyrido[1',2':4,5][1,-4]oxazino[2,3-b]quinoxaline and 1,2,3,4,4a,5-hexahydro-10-methoxypyrido[1',2':4,5][1,-4]oxazino[2,3-b]quinoxaline If 2,3-dichloro-6-methoxyquinoxaline is substituted for 2,3,6-trichloroquinoxaline in the procedure of Example 2, the above compounds are obtained.

EXAMPLE 21

N-(1,2,3,4,4a,5-hexahydropyrido[1',2':4,5][1,4]oxazino[2,3-b]quinoxaline-11-yl)benzamide A mixture of 5.1 g. of 11-amino-1,2,3,4,4a,5-hexahydropyrido[1',2':4,5][1,4]oxazino[2,3-b]quinoxaline, 100 ml. of methylene chloride and 20 ml. of 1 N sodium hydroxide is stirred and 2.8 g. of benzoyl chloride is added. The reaction mixture is stirred overnight and the layers are separated. The methylene chloride layer is washed with water and concentrated and N-(1,2,3,4,4a,5-hexahydropyrido[1',2':4,5][1,4]oxazino[2,3-b] quinoxalin-11-yl)benzamide is obtained.

EXAMPLE 22

9,10-Dichloro-1,2,3,4,4a,5-hexahydropyrido[1',2':4,5][1,4]oxazino[2,3-b]quinoxaline The above compound is obtained when 2,3,6,7-tetrachloro quinoxaline is treated with 2-piperidinomethanol by the procedure of Example 1.

EXAMPLE 23

9,10-Dibutoxy-1,2,3,4,4a,5-hexahydropyrido[1',2':4,5][1,4]oxazino[2,3-b]quinoxaline If 6,7-dibutoxy-2,3-dichloroquinoxaline is substituted for 2,3-dichloroquinoxaline in the procedure of Example 1, the above compound is obtained.

EXAMPLE 24

8,11-Dichloro-1,2,3,4,4a,5-hexahydropyrido[1',2':4,5][1,4]oxazino[2,3-b]quinoxaline This compound is obtained when 2,3,5,8-tetrachloroquinoxalinee is reacted with 2-piperidinomethanol by the procedure of Example 1.

EXAMPLE 25

8,11-Diethoxy-1,2,3,4,4a,5-hexahydropyrido[1',2':4,5][1,4]oxazino[2,3-b]quinoxaline When 2,3-dichloro-5,8-diethoxyquinoxaline is substitututed for 2,3-dichloroquinoxaline is the procedure of Example 1, the above compound is obtained.

EXAMPLE 26

1,2,3,4,4a,5-Hexahydropyrido[1',2':4,5][1,4]oxazino[2,3-b]quinoxaline

The above compound is obtained when 2,3-dibromoquinoxaline is treated with 2-piperidinomethanol by the procedure of Example 1.

We claim:

1. A compound selected from the group consisting of those of the formula:

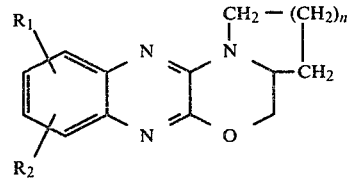

wherein n is the integer 1 or 2 and $R_1$ and $R_2$ are each individually selected from the group consisting of hydrogen, fluoro, chloro, bromo, trifluoromethyl, alkyl having up to 4 carbon atoms, alkoxy having up to 4 carbon atoms, nitro, amino, alkanoylamino having from 2 to 4 carbon atoms, benzoylamino and dimethylformamidino; and the pharmacologically acceptable acid-addition salts thereof.

2. The compound according to claim 1 wherein n is 1, $R_1$ is 10-methyl and $R_2$ is 8-acetylamino.

3. The compound according to claim 1 wherein n is 1, $R_1$ is 9-ethoxy and $R_2$ is 7-bromo.

4. The compound according to claim 1 wherein n is 1, and $R_1$ and $R_2$ are both hydrogen.

5. The compound according to claim 1 wherein n is 1, $R_1$ is hydrogen and $R_2$ is 8-chloro.

6. The compound according to claim 1 wherein n is 1, $R_1$ is 9-chloro and $R_2$ is hydrogen.

7. The compound according to claim 1 wherein n is 2, $R_1$ is 11-isobutyl and $R_2$ is 8-fluoro.

8. The compound according to claim 1 wherein n is 2, $R_1$ is 10-trifluoromethyl and $R_2$ is 9-benzoylamino.

9. The compound according to claim 1 wherein n is 2, and $R_1$ and $R_2$ are both hydrogen.

10. The compound according to claim 1 wherein n is 2, $R_1$ is hydrogen and $R_2$ is 9-chloro.

11. The compound according to claim 1 wherein n is 2, $R_1$ is 10-chloro and $R_2$ is hydrogen.

12. The process of preparing compounds of the formula:

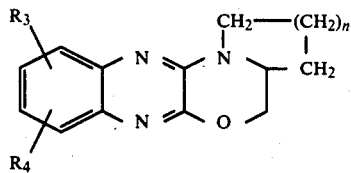

wherein n is the integer 1 or 2 and $R_3$ and $R_4$ are each individually selected from the group consisting of hydrogen, fluoro, chloro, bromo, trifluoromethyl, alkyl having up to 4 carbon atoms, alkoxy having up to 4 carbon atoms and nitro which comprises condensing a compound of the formula:

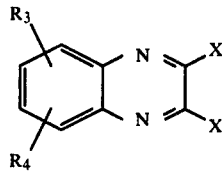

wherein X is chloro or bromo and $R_3$ and $R_4$ are as hereinbefore defined with 2-pyrrolidinomethanol or 2-piperidinomethanol in an inert organic solvent at 75°–100° C. for a period of time sufficient for a substantial degree of cyclization to occur.

* * * * *